United States Patent
Hardouin et al.

(10) Patent No.: US 8,212,077 B2
(45) Date of Patent: Jul. 3, 2012

(54) PROCESS FOR THE SYNTHESIS OF AGOMELATINE

(75) Inventors: Christophe Hardouin, Le Havre (FR);
Jean-Pierre Lecouve, Le Havre (FR);
Nicolas Baragnier, Rouen (FR)

(73) Assignee: Les Laboratoires Servier, Suresnes Cedex (FR)

( * ) Notice: Subject to any disclaimer, the term of this patent is extended or adjusted under 35 U.S.C. 154(b) by 514 days.

(21) Appl. No.: 12/462,469

(22) Filed: Aug. 4, 2009

(65) Prior Publication Data
US 2010/0036162 A1    Feb. 11, 2010

(30) Foreign Application Priority Data
Aug. 5, 2008   (FR) ..................... 08 04465

(51) Int. Cl.
*C07C 233/05* (2006.01)
*C07C 231/12* (2006.01)
(52) U.S. Cl. ..................................... 564/219
(58) Field of Classification Search ............. 564/219
See application file for complete search history.

(56) References Cited

U.S. PATENT DOCUMENTS
2011/0130571 A1   6/2011   Zhang et al.

FOREIGN PATENT DOCUMENTS
| | | |
|---|---|---|
| EP | 0447285 | 9/1991 |
| EP | 0962434 | 12/1999 |
| EP | 0994102 | 4/2000 |
| EP | 1564202 | 8/2005 |
| WO | WO2010012208 | 2/2010 |

OTHER PUBLICATIONS
French Preliminary Search Report for FR/08.04465 of Feb. 24, 2009.

*Primary Examiner* — Shailendra Kumar
(74) *Attorney, Agent, or Firm* — Hueschen and Sage

(57) ABSTRACT
Process for the industrial synthesis of the compound of formula (I)

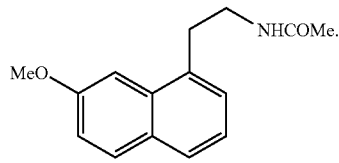

(I)

9 Claims, No Drawings

PROCESS FOR THE SYNTHESIS OF AGOMELATINE

The present invention relates to a new process for the industrial synthesis of agomelatine, or N-[2-(7-methoxy-1-naphthyl)ethyl]acetamide, of formula (I):

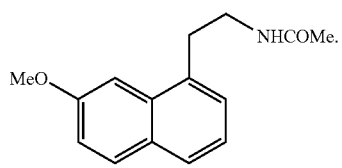
(I)

Agomelatine, or N-[2-(7-methoxy-1-naphthyl)ethyl]acetamide, has valuable pharmacological properties.

It has, in fact, the double characteristic of being, on the one hand, an agonist of receptors of the melatoninergic system and, on the other hand, an antagonist of the $5\text{-HT}_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European patent specifications EP 0 447 285 and EP 1 564 202.

In view of the pharmaceutical value of this compound, it has been important to be able to produce it using an effective industrial synthesis process which is readily transferable to the industrial scale and which provides agomelatine in a good yield and with excellent purity.

Patent specification EP 0 447 285 describes production of agomelatine in eight steps starting from 7-methoxy-1-tetralone, in an average yield of less than 30%.

In patent specification EP 1 564 202, the Applicant developed a new, much more effective and industrialisable synthesis route in only four steps starting from 7-methoxy-1-tetralone that makes it possible to obtain agomelatine in highly reproducible manner in a well-defined crystalline form.

However, the search for new synthesis routes, especially starting from starting materials that are less costly than 7-methoxy-1-tetralone, is currently still relevant.

The Applicant has continued his investigations and has developed a new process for the synthesis of agomelatine starting from 7-methoxy-1-naphthol: this new starting material has the advantage of being simple, readily obtainable in large quantities at less cost. 7-Methoxy-1-naphthol moreover also has the advantage of having a naphthalene ring system in its structure, which avoids inclusion of an aromatisation step in the synthesis, a step that is always problematic from an industrial point of view.

This new process moreover makes it possible to obtain agomelatine in reproducible manner and without requiring laborious purification, with a purity that is compatible with its use as a pharmaceutical active ingredient.

More specifically, the present invention relates to a process for the industrial synthesis of the compound of formula (I):

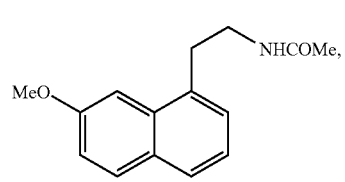
(I)

which process is characterised in that there is reacted 7-methoxy-1-naphthol of formula (II):

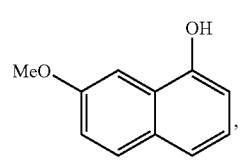
(II)

with which there is condensed, in the presence of palladium, after converting the hydroxy function into a leaving group such as a halogen, tosylate or trifluoromethanesulphonate group, the compound of formula (III): $CH_2=CH-R$ (III), wherein R represents the group

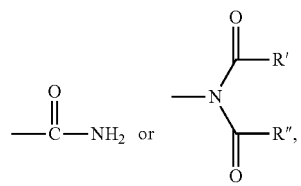

wherein R' and R", which may be the same or different, each represent a linear or branched $(C_1\text{-}C_6)$alkyl group or R' and R" together form a $(C_2\text{-}C_3)$alkylene chain and the ring formed may be fused with a phenyl group,
to yield the compound of formula (IV):

(IV)

wherein R is as defined hereinbefore,
which is subjected to catalytic hydrogenation to yield the compound of formula (V):

(V)

wherein R is as defined hereinbefore, which is subjected to base or acid hydrolysis or to a binary reducing agent/acid system to yield the compound of formula (VI) or its hydrochloride salt:

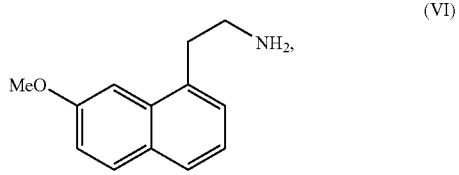

which is successively subjected to the action of sodium acetate and then acetic anhydride to yield the compound of formula (I), which is isolated in the form of a solid.

The compound of formula (III) according to the process of the invention is preferably a phthalimide compound, more preferably N-vinylphthalimide. Advantageously the compound of formula (III) is also acrylamide.

The condensation according to the invention of the compound of formula (III) to obtain the compound of formula (IV) is advantageously carried out using palladium tetrakis(triphenylphosphine); the reaction is preferably carried out at reflux of toluene.

The hydrogenation of the compound of formula (IV) into the compound of formula (V) is preferably carried out using palladium-on-carbon, more especially palladium-on-carbon with a minimum palladium content of 5%.

In advantageous manner, the hydrolysis of the compound of formula (V) is preferably carried out using a binary reducing agent/acid system such as, for example, NaBH$_4$ and then acetic acid or, when R represents a group C(O)NH$_2$, the conversion of the compound of formula (V) into the compound of formula (VI) is preferably carried out using a base such as, for example, NaOBr or NaOCl.

This process is especially valuable for the following reasons:
- it makes it possible to obtain the compound of formula (I) on an industrial scale in excellent yields, starting from a simple, low-cost starting material;
- the operating conditions selected according to the invention allow complete control of regioselectivity during coupling with the compound of formula (III);
- it makes it possible to avoid an aromatisation reaction because the naphthalene ring system is present in the starting substrate;
- finally, the compound of formula (I) obtained has, in reproducible manner, the characteristics of the crystalline form described in patent specification EP1564202.

The compounds of formula (IV) obtained according to the process of the invention are new and useful as intermediates in the synthesis of agomelatine, wherein they are subjected to a reduction reaction, then to a hydrolysis reaction and then to a coupling reaction with acetic anhydride.

The Examples hereinbelow illustrate the invention without limiting it in any way.

EXAMPLE 1

N-[2-(7-Methoxy-1-naphthyl)ethyl]acetamide

Step A: 7-Methoxy-1-naphthyl trifluoromethanesulphonate

In a reactor, 2.7 g of 7-methoxy-1-naphthol, 1.1 eq. of triflic anhydride and 1.1 eq. of 2,6-di-tert-butyl-4-methyl-pyridine are introduced into dichloromethane (45 ml). The mixture is heated at reflux for 12 hours and then filtered, and the liquors are washed with 1N HCl solution and then with saturated NaCl solution. The organic phase is evaporated and the residue obtained is purified by chromatography on silica gel (eluant: CH$_2$Cl$_2$/methyl-cyclohexane 1/9) to yield the title product in the form of an oil in a yield of 91% and with a chemical purity of more than 99%.

Step B: 2-[2-(7-Methoxy-1-naphthyl)ethenyl]-1H-isoindole-1,3(2H)-dione

In a reactor, 2 g of the compound obtained in Step A, 2 eq. of N-vinylphthalimide, 1.25 eq. of diisopropylethylamine and 0.05 eq. of palladium tetrakis(triphenylphosphine) are introduced into toluene and heated at reflux. The reaction is continued at reflux for 12 hours and then the reaction mixture is cooled to ambient temperature. Ethyl acetate is added, and then washings with water and 1N HCl solution are carried out. After evaporating off the solvents, the residue obtained is purified by chromatography on silica gel (eluant:dichloromethane/heptane 1/1, and then dichloromethane) to yield the title product in a yield of 80% and with a chemical purity of more than 95%.

Melting point: 146° C.

Step C: 2-[2-(7-Methoxy-1-naphthyl)ethyl]-1H-isoindole-1,3(2H)-dione

In a reactor, 2 g of the compound obtained in Step B and 1 g of 5% palladium-on-carbon are introduced into a methano/THF 1/2 mixture under hydrogen pressure and at ambient temperature. After reacting for 8 hours, the reaction mixture is filtered. After evaporating off the solvents, the title product is obtained quantitatively with a chemical purity of 95%.

Melting point: 154° C.

Step D: 2-(7-Methoxy-1-naphthyl)ethanamine

In a reactor, 1 g of the compound obtained in Step C and 5 eq. of NaBH4 are introduced into a 2-propanol/water 6/1 mixture, and the mixture is stirred at ambient temperature. Acetic acid (0.2 eq.) is then added and the reaction mixture is heated at 80° C. for 8 hours. After evaporating off the solvents and co-evaporation of water with toluene, the crude residue obtained is used directly in the acetylation reaction without further purification.

Step E:
N-[2-(7-Methoxy-1-naphthyl)ethyl]acetamide

In a reactor, 5 g of the compound obtained in Step D and 2 g of sodium acetate are introduced into ethanol. The mixture is stirred, 2.3 g of acetic anhydride are then added, the reaction mixture is heated to reflux and 20 ml of water are added. The reaction mixture is allowed to return to ambient temperature and the precipitate obtained is filtered off and washed with an ethanol/water 35/65 mixture to yield the title product in a yield of 80% for the two Steps D and E and with a chemical purity of more than 99%.

Melting point: 108° C.

EXAMPLE 2

N-[2-(7-Methoxy-1-naphthyl)ethyl]acetamide

Step A: 3-(7-Methoxy-1-naphthyl)-2-propenamide

A solution of the compound obtained in Step A of Example 1 (12.1 g) in 80 mL of DMF is degassed by bubbling in nitrogen for 10 minutes at 20° C. To the resulting solution there are successively added triethylamine (6.6 mL), acrylamide (5.6 g), neocuproine hydrate (454 mg) and Pd(OAc)$_2$ (445 mg).

The mixture is heated for 1 hour at 100° C. and then allowed to cool to 20° C. After dilution with AcOEt (100 mL) and then addition of saturated NH$_4$Cl solution, the phases are separated. The organic phase is concentrated under reduced pressure and the residue diluted in AcOEt (50 mL). The precipitate is filtered to yield the title product in the form of a powder.

Step B: 3-(7-Methoxy-1-naphthyl)propanamide 0.12 g of 5% Pd/C (50% wet) is added to a solution of the compound obtained in Step A (0.5 g) in a mixture of MeOH (6.5 mL)/THF (6.5 mL). The mixture is purged with nitrogen and then with hydrogen before being heated at 50° C. under atmospheric pressure during 1 hour. The suspension is then filtered over Celite and the filter is washed with a mixture of MeOH (5 mL)/THF (5 mL). The liquors are concentrated under reduced pressure to yield the title product in the form of a solid which is directly engaged in the following step without further purification.

Step C: 2-(7-Methoxy-1-naphthyl)ethanamine hydrochloride

Iodosobenzene diacetate (0.88 g) is added to a solution of water (3 mL)/acetonitrile (3 mL). After stirring for 10 minutes at 20° C., the compound obtained in Step B (500 mg) is added in portions and then the mixture is left at 20° C. for 2 hours. After the starting material has been consumed, the acetonitrile is distilled off under reduced pressure. The residue is taken up H$_2$O (10 mL) and then treated with concentrated HCl solution (0.4 mL). After filtration, the precipitate obtained is washed with ethyl acetate and then dried in an oven to yield the title product.

Melting point: 243° C.

Step D: N-[2-(7-Methoxy-1-naphthyl)ethyl]acetamide

In a reactor, 5 g of the compound obtained in Step C and 2 g of sodium acetate are introduced into ethanol. The mixture is stirred, 2.3 g of acetic anhydride are then added, the reaction mixture is heated to reflux and 20 ml of water are added. The reaction mixture is allowed to return to ambient temperature and the precipitate obtained is filtered off and washed with an ethanol/water 35/65 mixture to yield the title product.

Melting point: 108° C.

EXAMPLE 3

Determination of the crystalline form of the compound N-[2-(7-methoxy-1-naphthyl)ethyl]acetamide obtained in Examples 1 and 2

Data recording was carried out using the D8 high-resolution diffractometer from Bruker AXS with the following parameters: an angular range of 3°-90° in terms of 2θ, a step of 0.01° and 30 s per step. The N-[2-(7-methoxy-1-naphthyl) ethyl]acetamide powder obtained in Examples 1 and 2 was deposited on a transmission mounting support. The X-ray source is a copper tube (λCuK$_{α1}$=1.54056 Å). The mounting includes a front monochromator (Ge(111) crystal) and an energy-resolved solid-state detector (MXP-D1, Moxtec-SEPH). The compound is well crystallised: the line width at half-height is of the order of 0.07° in terms of 2θ.

The following parameters were accordingly determined:

crystal structure of unit cell: monoclinic, unit cell parameters: a=20.0903 Å, b=9.3194 Å, c=15.4796 Å, β=108.667° space group: P2$_1$/n number of molecules in the unit cell: 8 volume of the unit cell: V$_{unit\ cell}$=2746.742 Å$^3$ density: d=1.13 g/cm$^3$.

EXAMPLE 4

Determination, by means of the X-ray powder diffraction diagram, of the crystalline form of the N-[2-(7-methoxy-1-naphthyl)ethyl]acetamide compound obtained in Examples 1 and 2

The crystalline form of the compound obtained in Examples 1 and 2 is characterised by the following X-ray powder diffraction diagram, measured using a Siemens D5005 diffractometer (copper anticathode) and expressed in terms of interplanar distance d, Bragg's angle 2 theta, and relative intensity (expressed as a percentage in relation to the most intense line):

| Angle 2 theta (°) | Interplanar distance d (Å) | Intensity (%) |
|---|---|---|
| 9.26 | 9.544 | 23 |
| 10.50 | 8.419 | 13 |
| 15.34 | 5.771 | 24 |
| 17.15 | 5.165 | 100 |

The invention claimed is:

1. A process for the synthesis of a compound of formula (I)

wherein 7-methoxy-1-naphthol of formula (II):

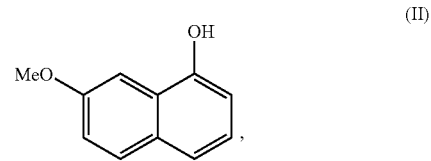

is subjected to appropriate reaction conditions to convert the hydroxy function into a leaving group and then condensed, in the presence of palladium, with a compound of formula (III): CH$_2$=CH—R (III), wherein R represents

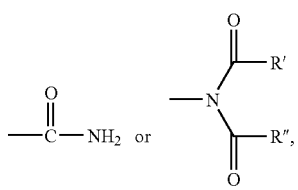

wherein R' and R", which may be the same or different, each represent a linear or branched ($C_1$-$C_6$)alkyl group or R' and R" together form a ($C_2$-$C_3$)alkylene chain and the ring formed may be fused with a phenyl group, to yield a compound of formula (IV):

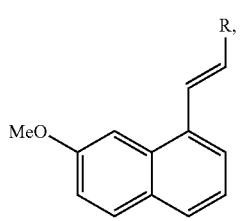

wherein R is as defined hereinbefore, which is subjected to catalytic hydrogenation to yield a compound of formula (V):

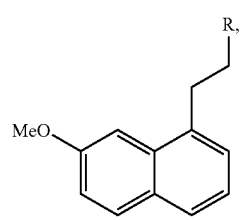

wherein R is as defined hereinbefore, which is subjected to base or acid hydrolysis or to a binary reducing agent/acid system to yield a compound of formula (VI) or its hydrochloride salt:

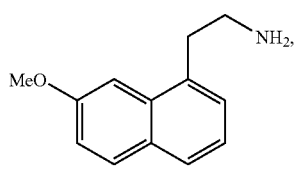

which is successively subjected to the action of sodium acetate and then acetic anhydride to yield the compound of formula (I), which is isolated in the form of a solid.

2. The process of claim 1, wherein the hydroxy function of 7-methoxy-1-naphthol of formula (II) is converted into a leaving group selected from halogen, tosylate and trifluoromethanesulphonate.

3. The process of claim 1, wherein the compound of formula (III) is N-vinylphthalimide.

4. The process of claim 1, wherein the compound of formula (III) is acrylamide.

5. The process of claim 1, wherein the condensation of the compound of formula (III) to obtain the compound of formula (IV) is carried out using palladium tetrakis(triphenylphosphine).

6. A compound selected from those of formula (IV):

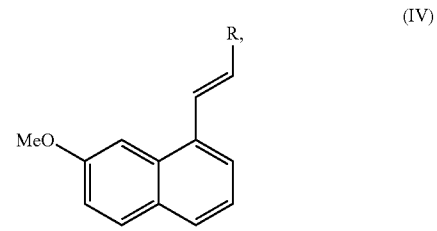

wherein R represents

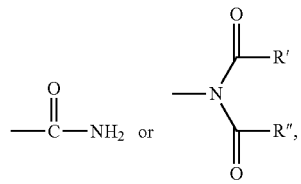

wherein R' and R", which may be the same or different, each represent a linear or branched ($C_1$-$C_6$)alkyl group or R' and R" together form a ($C_2$-$C_3$)alkylene chain and the ring formed may be fused with a phenyl group.

7. A process for the synthesis of agomelatine of formula (I)

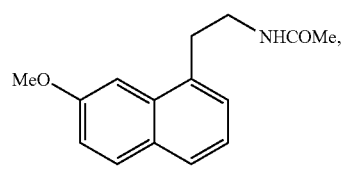

starting from a compound of formula (IV)

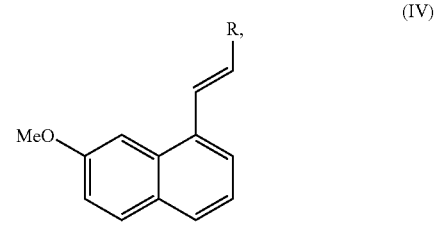

wherein R represents

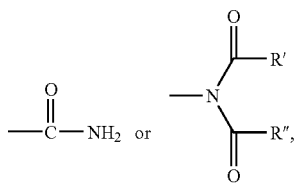

wherein R' and R", which may be the same or different, each represent a linear or branched ($C_1$-$C_6$)alkyl group or R' and R" together form a ($C_2$-$C_3$)alkylene chain and the ring formed may be fused with a phenyl group, wherein the compound of formula (IV) is obtained by the process of claim 1.

8. A process for the synthesis of agomelatine of formula (I)

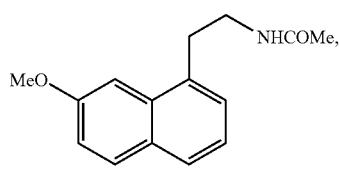

(I)

starting from a compound of formula (V)

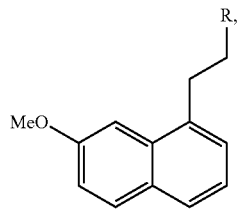

(V)

wherein R represents

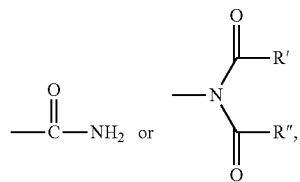

wherein R' and R", which may be the same or different, each represent a linear or branched ($C_1$-$C_6$)alkyl group or R' and R" together form a ($C_2$-$C_3$)alkylene chain and the ring formed may be fused with a phenyl group, wherein the compound of formula (V) is obtained by the process of claim 1.

9. A process for the synthesis of agomelatine of formula (I)

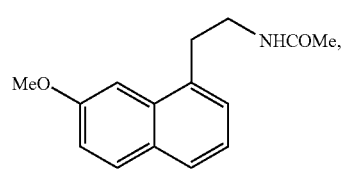

(I)

starting from a compound of formula (VI)

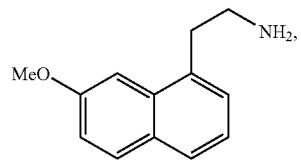

(VI)

wherein the compound of formula (VI) is obtained by the process of claim 1.

* * * * *